United States Patent [19]

Goldberg et al.

[11] Patent Number: 4,578,219

[45] Date of Patent: Mar. 25, 1986

[54] ANTIGENIC PEPTIDE COMPOUND

[75] Inventors: Erwin Goldberg, Evanston, Ill.; Thomas E. Wheat, Chicago, Ill.

[73] Assignee: Northwestern University, Evanston, Ill.

[21] Appl. No.: 663,058

[22] Filed: Oct. 19, 1984

[51] Int. Cl.$^4$ ............................................. C07C 103/52
[52] U.S. Cl. ............................................. 260/112.5 R
[58] Field of Search ................................. 260/112.5 R

[56] References Cited

U.S. PATENT DOCUMENTS 4,290,944  9/1981  Goldberg .................. 260/112.5 R
4,353,822 10/1982  Goldberg .................. 260/112.5 R
4,392,997  7/1983  Goldberg .................. 260/112.5 R Primary Examiner—Delbert R. Phillips

[57] ABSTRACT

The novel antigenic linear peptide of this invention comprise a linear peptide of 13 amino acids, comprising the sequence Val-Asn-Met-Thr-Ala-Gly-Glu-Glu-Gly-Leu-Leu-Lys-Lys. This compound corresponds with the amino acids 304 to 316 of mouse LDH-C$_4$. The compound has utility in vaccines for reducing the fertility of female mammals.

1 Claim, No Drawings

ANTIGENIC PEPTIDE COMPOUND

GRANT REFERENCE

This invention was developed in part under Grant HD 05863 by the National Institutes of Health.

BACKGROUND AND PRIOR ART

Mammalian spermatozoa have been known to be antigenic for many years. More recently, it has been demonstrated that mammalian sperm contain an antigenic enzyme, which is known as the $C_4$ isozyme of lactate dehydrogenase, (LDH-$C_4$) LDH-$C_4$ has been isolated in pure crystalline form from mouse testes. Goldberg (1972) *J. Biol. Chem.* 247:2044-2048. The enzyme has a molecular weight of 140,000 and is composed of four identical C subunits. The amino acid sequence and three-dimensional structure of LDH-$C_4$ has been described by several investigators: Musick et al (1976) *J. Mol. Biol.* 104:659-668; Wheat et al (1977) *Biochem & Biophys. Res. Comm.* 74:1066-1077; Li et al (1983) *J. Biol. Chem.* 258:7017-7028; and Pan et al (1983) 258:7005-7016 *J. Biol. Chem.*

In 1974, Dr. Erwin Goldberg reviewed the effects of immunization with LDH-$C_4$ on fertility, and advanced the possibility that "by using a defined macromolecular constituent of sperm it becomes possible to elucidate its primary structure in terms of amino acid sequence, to map specifically the antigenic determinant(s) responsible for inducing infertility, and then to construct synthetic peptides containing these determinants. Possessing the capability for synthesizing a molecule with such properties, making the immunological approach to fertility control feasible. *Karolinska Symposia on Research Methods in Reproductive Endrocrinology*, 7th Symposia: Immunological Approaches to Fertility Control, Geneva, 1974 202-222.

Subsequent investigations by Dr. Goldberg and his research associates have identified several amino acid sequences of mouse LDH-$C_4$ which in isolated form (e.g., as short chain peptides) bind to LDH-$C_4$ antiserum. Wheat et al (1981), in Rich et al, *Peptides: Synthesis-Structure-Function, Proc. 7th Amer. Peptide Symp.*, pp. 557-560; and Gonzales-Prevatt et al (1982) *Mol. Immunol.* 19:1579-1585. Antigenic peptide compounds based on the Goldberg sequences have been patented. See U.S. Pat. Nos. 4,290,944; 4,310,456; 4,353,822; 4,377,516; and 4,392,997.

These antigenic peptides are useful in preparing vaccines to reduce female fertility. Immunization of female mammals results in the development of circulating antibodies specific to LDH-$C_4$. These immunoglobins reach the female reproductive tract as a transudate of serum. Kille et al (1977), *Biol. Reprod.* 20:863-871. Antibody in cervical mucus, uterine fluids and oviducal fluids combines with LDH-$C_4$ on the sperm surface and impedes the progress of the male gamete, presumably by agglutination. Systemic immunization with LDH-$C_4$ markedly interferes with sperm transport in the female reproductive tract. Kille et al (1980) *J. Reprod. Immunol.* 2:15-21.

The current status of research on LDH-$C_4$ and antigenic peptides for use in female contraceptive vaccines are summarized in two recent publications by the Goldberg group: Goldberg et al (1983), In *Immunology of Reproduction*, Chapt. 22, pp. 493-504; and Wheat et al (1983), In *Isozymes: Current Topics in Biological and Medical Research*, Vol. 7, pp. 113-140.

The search for additional antigenic peptides containing antibody binding sequences of mouse LDH-$C_4$ has continued. While it is known that this isozyme contains multiple antigenic domains, there is no recognized basis for locating such domains nor for predicting their effectiveness for binding antibodies to LDH-$C_4$ or for generating antibodies in female mammals capable of interfering with sperm transport. The effectiveness of immunocontraception by this route probably depends upon sufficiently high concentrations of antibodies in the reproductive tract. To date, laboratory trial and error experimentation has been the only available approach.

SUMMARY OF INVENTION

A new antigenic peptide compound binding to LDH-$C_4$ antisera has now been discovered. The 13 amino acid peptide comprises the linear sequence Val-Asn-Met-Thr-Ala-Gly-Glu-Glu-Gly-Leu-Leu-Lys-Lys. This sequence is believed to correspond to amino acids MC 304-316 in mouse LDH-$C_4$, as sequenced by Li et al (1983) *J. Biol. Chem.* 258:7017-7028. The peptide compound of this invention may include other amino acids of LDH-$C_4$ connecting with and including the above sequence, or shorter segments thereof including the antigenic domain, which are believed to be multiple. This compound can be used to prepare vaccines for reducing the fertility of female mammals including woman, since mouse LDH-$C_4$ is homologous with human LDH-$C_4$.

DETAILED DESCRIPTION

Standard abbreviations and symbols will be used herein to designate the amino acid present in the peptide compound of this invention. These are:

| Amino Acids | Abbreviations | Symbols |
| --- | --- | --- |
| L-alanine | Ala | A |
| L-asparagine | Asn | N |
| L-aspartic acid | Asp | D |
| L-glutamic acid | Glu | E |
| glycine | Gly | G |
| L-leucine | Leu | L |
| L-lysine | Lys | K |
| L-methionine | Met | M |
| L-threonine | Thr | T |
| L-valine | Val | V |

The antigenic peptide compound of this invention comprises the compound corresponding to the amino acid sequence MC 304 to 316 of mouse LDH-$C_4$ or segments thereof including the antigenic domain or domains thereof. More specifically the compound is represented by the sequence: V-N-M-T-A-G-E-E-G-L-L-K-K. The above formula represents a linear peptide shown in left to right representation, the N-terminal amino acid being on the left side and the C-terminal amino acids being on the right side. All of the amino acids represented are L-amino acid with the exception of glycine (G) which has only one form.

The peptide compound of the present invention can be synthesized from its constituent amino acids. For example, the synthesis can be carried out by the Merrifield solid phase method, as described in *J.A.C.S.* 85:2149-2154 (1963). This solid phase method for synthesizing sequences of amino acids is also described in Stewart and Young, *Solid Phase Peptide Synthesis* (W. H. Freeman and Co., San Francisco, 1969), pages 1–4. In this procedure, the C-terminal amino acid is attached to chloromethylated polystyrene-divinylbenzene copolymer beads. Each subsequent amino acid, with suitable protecting group, is then added sequentially to the growing chain. For example, as described in the Merrifield article, the protective group may be a carbobenzoxy group. By the procedure of coupling, deprotection, and coupling of the next amino acid, the desired amino acid sequence and chain length can be produced. As a final step, the protective group is removed from the N-terminal amino acid (viz., lysine) and the C-terminal amino acid is cleaved from the resin, using a suitable reagent, such as trifluoroacetic acid and hydrogen bromide. Since this synthesis procedure is well known, it is not believed that it will be necessary to further describe it herein.

To utilize the antigenic peptide of this invention in the form of a fertility reducing vaccine, the peptide is conjugated to a carrier molecule, which is preferably a protein which itself elicits an antigenic response and which can be safely administered. For example, the peptide can be coupled to tetanus toxoid for administration by intramuscular injection. For example, a mixture of 1, uMole tetanus toxoid, 60, uMoles antigenic peptide, and 18 millimoles 1-ethyl-ε-(3 dimethyl aminopropyl) carbodiimide hydrochloride reacted in water (pH6) for 12 hours at room temperature and 24 hours at 4° gives a product containing 3.5 moles of peptide/mole tetanus toxoid. Excess reactants can be removed by dialysis or gel filtration. See Pique et al, *Immunochemistry*, 15:55–60 (1978). Alternatively, the peptide may be coupled using bisdiazotized benzidine (Bassiri et al, *Endocrinology*, 90:722 (1972) or glutaraldehyde. To facilitate coupling to a protein an additional amino acid such as cysteine may be attached to the N-terminal valine. For example, the compound prepared in a form for coupling would be: N-Cys-Val-Asn-Met-Thr-Ala-Gly-Glu-Glu-Gly-Leu-Leu-Lys-Lys.

For intramuscular injection, the coupled peptide may be suspended in a sterile isotonic saline solution, or other conventional vehicle, and, if desired, an adjuvant may be included. A preferred use of such a vaccine is for administration to human females. Antibodies will be formed, which will appear in the oviduct fluids and thereby achieve a significant reduction in fertility. For this purpose, the amount to be administered will range from about 1 to 10 milligrams (mg) of the antigenic peptide.

The compounds of this invention and their antigenic properties are further illustrated by the following examples.

EXAMPLE I

The purification of peptides by reverse phase high performance liquid chromatography has been described by Wheat et al (1981), cited above. Pure mouse LDH-C$_4$ is reduced and carboxymethylated with iodoacetic acid. Digestion with trypsin (4% w/w) proceeds for 4 hours in the presence of 2 M urea. After desalting on Sephadex G-10, the digest is fractionated on a ,uBondapak C$_{18}$ column (3.9 mm×30 cm; Waters Associates) with a gradient of increasing acetonitrile. Trifluoracetic acid (0.04%) is present throughout the gradient. The column effluent is monitored at 214 nm, and fractions are collected manually based on peak absorbance. Fractions are dried under a stream of nitrogen and lyophilized from water. Purity is assessed isocratically in the same chromatographic system, and peptides are repurified as necessary. Following hydrolysis (6 N HCl, 107°, 40 hrs.), amino acid compositions are determined with reverse phase chromatography of o-pthalaldehyde derivatives. See Hill, et al. (1979) *Anal Chem.* 51:1338–1341. Amino acid sequences were established by the manual Edman degradation. See Tarr (1977) in *Methods in Enzymology*, Vol. 47, pp. 335–357; and Tarr (1981) *Anal. Biochem.* 111:27–32.

Following this procedure a segment was obtained which was later determined to be the sequence Val-Asn-Met-Thr-Ala-Gly-Glu-Glu-Gly-Leu-Leu-Lys-Lys. The peptide was tested for antibody binding activity as follows:

Antibody binding by the purified peptide was assessed with a solid matrix radioimmunoassay. The peptide was coated on the walls of a polyvinyl chloride microtiter plate by incubating, overnight at 4° C., a solution containing 5 nmoles of peptide in 100, ul of 0.05 M NaPO$_4$, 0.14 M Na Cl (PBS) in each well. Each well was washed with 200 Ml/well 10% horse serum in PBS and incubated for 1 hour in the same solution. After washing, the plate was incubated with 50, ul of the gamma-globulin fraction of pooled rabbit antimouse LDH-C$_4$ sera. After 4-hours incubation, the plate was washed and then incubated with 100, ul/well of $^{125}$I-goat antirabbit gamma-globulin for 16 hours at 4° C. After exhaustive washing, bound radioactivity was determined using a gamma counter.

EXAMPLE II

Synthesis of the peptide Val-Asn-Met-Thr-Gly-Glu-Glu-Gly-Leu-Leu-Lys-Lys can be carried out employing solid phase techniques now well known in the art. In a preferred procedure amino protected lysine, representing the -COOH terminal group of the above peptide, is coupled to a conventional solid phase peptide synthesis resin such as chloromethyl polystyrene cross-linked with 1 to 2% divinyl benzene. The amino protecting group is then selectively removed utilizing a suitable reagent whose nature will depend on the protecting group used. In the preferred embodiment the t-butyloxycarbonyl (Boc) group is utilized for amino group protection and 40% trifluoracetic acid in methylene chloride is the selective deprotecting agent.

After deprotection, the lysine is treated with protected lysine, preferably αBoc- εcarbobenzoxy-L-lysine, and dicyclohexycarbodiimide in a manner known per se as to form a peptide bond between the free amino group of the lysine residue and the carboxyl group of protected lysine.

The cycle of deprotection and coupling with amino acid derivatives and dicyclohexylcarbodiimide is then repeated with the remaining amino acids in the sequence order of the above peptide. Some of the amino acids required side-chain blocking groups besides the alpha-amino protection. Such amino acids and the blocking groups are as follows:

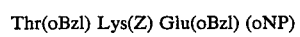

Thr(oBzl) Lys(Z) Glu(oBzl) (oNP)

where Bzl is benzyl and N is nitrophenyl and Z is ε-carbobenzoxy.

Completion of the synthesis provided the following tridecapeptide coupled to the styrenedivinylbenzene copolymer resin:

Val-Asn(oNP)-Met-Thr(Bzl)-Ala-Gly-Glu(oBzl)-
Glu(oBzl)-Gly-Leu-Leu-Lys(Z)-Lys(Z).

Decoupling of the peptide from the resin is accomplished by treatment with liquid hydrogen flouride with concomitant cleavage of all protecting groups to produce the desired peptide.

The antibody binding activity of the peptide, prepared as described, can be determined as described in Example I.

We claim:
1. The antigenic peptide compound binding to LDH-$C_4$ antisera represented by the sequence of N-terminal to C-terminal amino acids, comprising V-N-M-T-A-G-E-E-G-L-L-K-K, wherein G represents glycine, and V, N, M, T, A, E, G, L, and K respectively represent the L-amino acid forms of valine, asparetic acid, methionine, threonine, alanine, glutamic acid, leucine, and lysine.

* * * * *